(12) United States Patent
Malcmacher et al.

(10) Patent No.: US 7,264,471 B2
(45) Date of Patent: *Sep. 4, 2007

(54) METHODS AND KITS FOR BLEACHING TEETH WHILE PROTECTING ADJACENT GINGIVAL TISSUE

(75) Inventors: Louis J. Malcmacher, Cleveland, OH (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 271 days.

This patent is subject to a terminal disclaimer.

(21) Appl. No.: 10/839,419

(22) Filed: May 5, 2004

(65) Prior Publication Data

US 2005/0249677 A1  Nov. 10, 2005

(51) Int. Cl.
*A61C 5/00* (2006.01)

(52) U.S. Cl. .................. 433/215; 433/216; 433/217.1; 424/53; 424/401

(58) Field of Classification Search .................. None
See application file for complete search history.

(56) References Cited

U.S. PATENT DOCUMENTS

| | | | |
|---|---|---|---|
| 165,584 A | 7/1875 | Hopfen | |
| 1,637,153 A | 7/1927 | Lawton | |
| 2,257,709 A | 9/1941 | Anderson | |
| 2,835,628 A | 5/1958 | Saffir | |
| 3,339,547 A | 9/1967 | Drabkowski | |
| 3,527,219 A | 9/1970 | Greenberg | |
| 3,624,909 A | 12/1971 | Greenberg | |
| 3,688,406 A | 9/1972 | Porter et al. | |
| 3,955,281 A | 5/1976 | Weitzman | |
| 4,064,628 A | 12/1977 | Weitzman | |
| 4,138,814 A | 2/1979 | Weitzman | |
| RE33,093 E | 10/1989 | Schiraldi et al. | |
| 4,900,721 A | 2/1990 | Bansemir | |
| 4,902,227 A | 2/1990 | Smith | |
| 5,008,093 A | 4/1991 | Merianos | |
| 5,085,585 A | 2/1992 | Zimble | |
| 5,108,742 A | 4/1992 | Merianos | |
| 5,112,225 A | 5/1992 | Diesso | |
| 5,183,901 A | 2/1993 | Login et al. | |
| 5,211,559 A | 5/1993 | Hart et al. | |
| 5,310,563 A | 5/1994 | Curtis et al. | |
| 5,326,685 A | 7/1994 | Gaglio et al. | |
| 5,346,061 A | 9/1994 | Newman et al. | |
| 5,356,291 A | 10/1994 | Darnell | |
| 5,376,006 A * | 12/1994 | Fischer .................. | 433/215 |
| 5,425,953 A | 6/1995 | Sintov et al. | |
| 5,562,449 A | 10/1996 | Jacobs et al. | |
| 5,573,399 A | 11/1996 | McClintock, II | |
| 5,575,654 A | 11/1996 | Fontenot | |
| 5,611,687 A | 3/1997 | Wagner | |
| 5,616,027 A | 4/1997 | Jacobs et al. | |
| 5,639,445 A | 6/1997 | Curtis et al. | |
| 5,702,251 A | 12/1997 | McClintock, II | |
| 5,707,235 A | 1/1998 | Knutson | |
| 5,711,935 A | 1/1998 | Hill et al. | |
| 5,769,633 A | 6/1998 | Jacobs et al. | |
| 5,816,802 A | 10/1998 | Montgomery | |
| 5,846,058 A | 12/1998 | Fischer | |
| 5,863,202 A * | 1/1999 | Fontenot et al. ............. | 433/215 |
| 5,879,691 A | 3/1999 | Sagel et al. | |
| 5,891,453 A | 4/1999 | Sagel et al. | |
| 5,894,017 A | 4/1999 | Sagel et al. | |
| 5,895,218 A | 4/1999 | Quinn et al. | |
| 5,922,307 A | 7/1999 | Montgomery | |
| 5,924,863 A | 7/1999 | Jacobs et al. | |
| 5,980,249 A | 11/1999 | Fontenot | |
| 5,989,569 A | 11/1999 | Dirksing et al. | |
| 6,045,811 A | 4/2000 | Dirksing et al. | |
| 6,080,397 A | 6/2000 | Pfirrmann | |
| 6,086,370 A * | 7/2000 | Jensen et al. ................ | 433/136 |
| 6,089,869 A | 7/2000 | Schwartz | |
| 6,096,328 A | 8/2000 | Sagel et al. | |
| 6,106,293 A | 8/2000 | Wiesel | |
| 6,126,443 A | 10/2000 | Burgio | |
| 6,136,297 A | 10/2000 | Sagel et al. | |
| 6,142,780 A | 11/2000 | Burgio | |
| 6,155,832 A | 12/2000 | Wiesel | |
| 6,183,251 B1 | 2/2001 | Fischer | |
| 6,197,331 B1 | 3/2001 | Lerner et al. | |
| 6,247,930 B1 | 6/2001 | Chiang et al. | |
| 6,254,391 B1 * | 7/2001 | Darnell ....................... | 433/216 |
| 6,274,122 B1 | 8/2001 | McLaughlin | |
| 6,277,458 B1 | 8/2001 | Dirksing et al. | |
| 6,280,196 B1 | 8/2001 | Berghash | |
| 6,287,120 B1 | 9/2001 | Wiesel | |
| 6,322,360 B1 | 11/2001 | Burgio | |
| 6,331,292 B1 | 12/2001 | Montgomery | |

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Frederick Krass
*Assistant Examiner*—Lezah Roberts
(74) *Attorney, Agent, or Firm*—Workman Nydegger

(57) ABSTRACT

Dental bleaching methods and kits employ a dental bleaching composition, a protective composition and a barrier layer. The dental bleaching composition is positioned so as to contact a person's tooth surfaces. The protective composition is positioned so as to shield a person's gingival tissue from the bleaching composition during tooth bleaching. The barrier layer protects at least the bleaching composition from saliva and/or mechanical forces during tooth bleaching. The dental bleaching composition and protective composition can be in the form of a sticky and viscous gel. The protective composition may alternatively be a flexible polymerizable material. The barrier layer may be a substantially flat sheet, strip or patch, or it may comprise a dental tray.

29 Claims, 8 Drawing Sheets

U.S. PATENT DOCUMENTS

| | | |
|---|---|---|
| 6,343,932 B1 | 2/2002 | Wiesel |
| 6,419,903 B1 | 7/2002 | Xu et al. |
| 6,419,906 B1 | 7/2002 | Xu et al. |
| 6,435,873 B1 | 8/2002 | Burgio |
| 6,440,396 B1 | 8/2002 | McLaughlin |
| 6,458,380 B1 | 10/2002 | Leaderman |
| 6,461,158 B1 | 10/2002 | Sagel et al. |
| 6,488,914 B2 | 12/2002 | Montgomery |
| 6,497,575 B2 | 12/2002 | Zavitsanos et al. |
| 6,500,408 B2 | 12/2002 | Chen |
| 6,503,486 B2 | 1/2003 | Xu et al. |
| 6,506,053 B2 | 1/2003 | Wiesel |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,649,147 B1 | 11/2003 | Ye et al. |
| 6,682,721 B2 | 1/2004 | Kim et al. |
| 6,689,344 B2 | 2/2004 | Chang et al. |
| 6,730,316 B2 | 5/2004 | Chen |
| 2001/0046654 A1 | 11/2001 | Zavitsanos et al. ........... 433/32 |
| 2002/0006387 A1 | 1/2002 | Sagel et al. .................... 424/53 |
| 2002/0006388 A1 | 1/2002 | Sagel et al. .................... 424/53 |
| 2002/0012685 A1 | 1/2002 | Sagel et al. .................. 424/401 |
| 2002/0018754 A1 | 2/2002 | Sagel et al. .................... 424/49 |
| 2002/0081555 A1 | 6/2002 | Wiesel ....................... 433/215 |
| 2002/0164292 A1 | 11/2002 | Peterson et al. ............... 424/53 |
| 2002/0182154 A1 | 12/2002 | McLaughlin .................. 424/53 |
| 2002/0187111 A1 | 12/2002 | Xu et al. ....................... 424/53 |
| 2002/0187112 A1 | 12/2002 | Xu et al. ....................... 424/53 |
| 2003/0003421 A1 | 1/2003 | Besenheider et al. ....... 433/215 |
| 2003/0012747 A1 | 1/2003 | Peterson ...................... 424/53 |
| 2003/0036037 A1 | 2/2003 | Zavitsanos et al. ......... 433/215 |
| 2003/0044631 A1 | 3/2003 | Sagal et al. ................. 428/548 |
| 2003/0068284 A1 | 4/2003 | Sagel et al. ................... 424/53 |
| 2003/0068601 A1 | 4/2003 | Zavitsanos et al. ......... 433/215 |
| 2003/0072722 A1* | 4/2003 | Nathoo ........................ 424/52 |
| 2003/0082114 A1 | 5/2003 | Kim et al. ..................... 424/53 |
| 2003/0133884 A1 | 7/2003 | Chang et al. .................. 424/53 |
| 2003/0194382 A1 | 10/2003 | Chang et al. .................. 424/53 |
| 2003/0198606 A1 | 10/2003 | Kim et al. ..................... 424/53 |

* cited by examiner

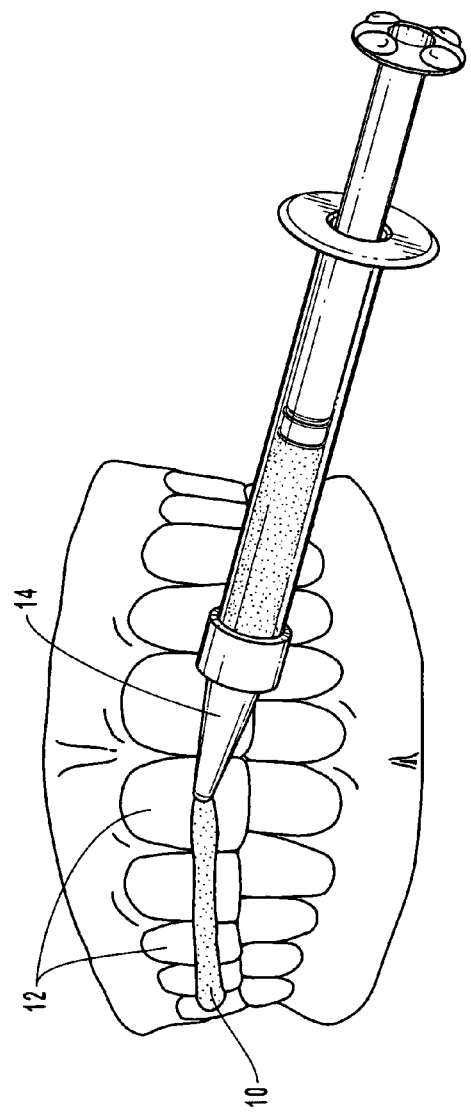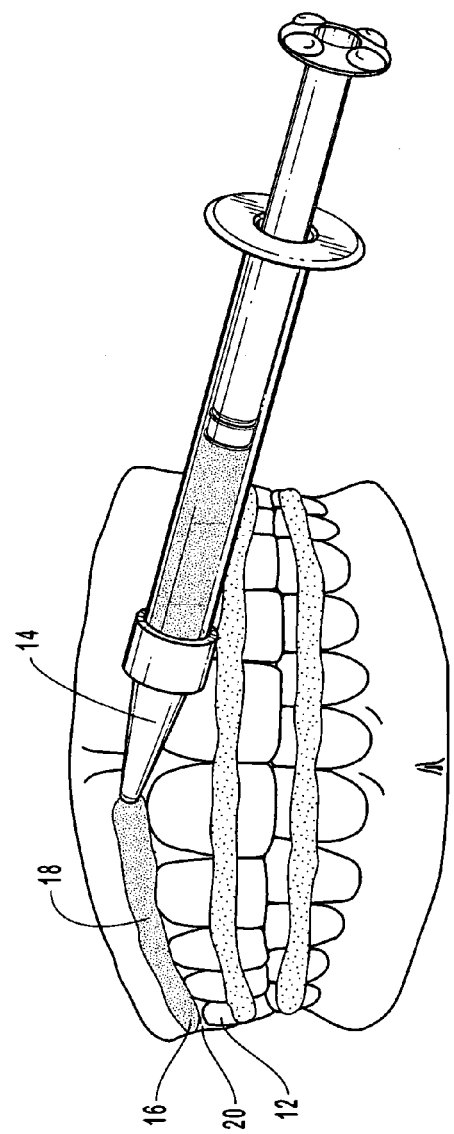

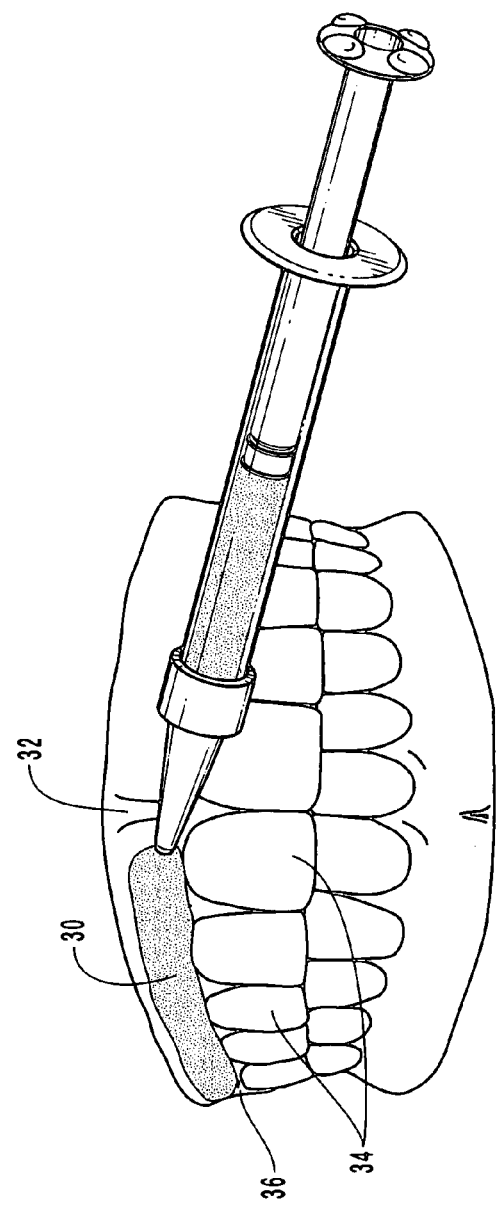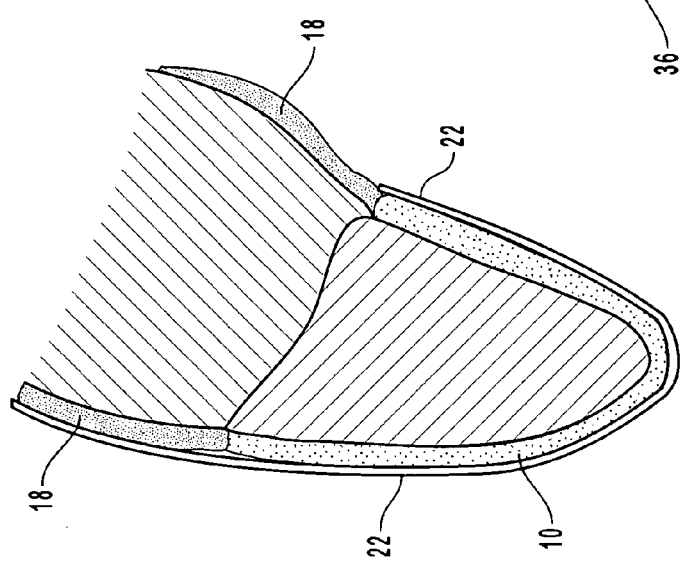

METHODS AND KITS FOR BLEACHING TEETH WHILE PROTECTING ADJACENT GINGIVAL TISSUE

BACKGROUND OF THE INVENTION

1. The Field of the Invention

This invention is in the field of dental bleaching. More particularly, the invention relates to methods and kits for bleaching a person's teeth using a dental bleaching composition while protecting adjacent soft oral tissue using a protective composition, together with a moisture-resistant barrier layer.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another bleaching method involves painting a bleaching composition directly onto a person's teeth. A perceived advantage of paint-on bleaching is that it eliminates the need for a dental tray. The main disadvantage of a paint-on bleaching composition is that it remains directly exposed to the person's saliva and disruptive forces found in a person's mouth. As a result, a significant portion of the bleaching composition does not remain on the teeth where bleaching is desired. Some or all of the composition can dissolve away into the person's saliva and/or be transferred to adjacent oral tissues, potentially irritating soft oral tissues.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces. Like paint-on bleaching compositions, this procedure does not require the use of dental trays. Unlike paint-on bleaching compositions, bleaching strips include a plastic barrier that, at least in theory, keeps the dental bleaching gel from diffusing into the user's mouth.

In reality, because of the generally poor adhesion of bleaching strips to the user's teeth, coupled with their generally flimsy nature, it is often difficult for the user to maintain the bleaching strip in its proper position for the recommended time. Conventional bleaching strips are prone to slip off the teeth as a result of even minimal movement of the user's mouth, jaw or tongue. Indeed, it is recommended that the user not eat, drink, smoke or sleep while wearing the bleaching strip. In practice, it is difficult to talk or smile while properly maintaining the bleaching strip in the correct position.

Even if a user successfully maintains a conventional bleaching strip in its proper position during the recommended bleaching period, the bleaching gel often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

In the case of home-use bleaching products, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen.

An alternative to home-use bleaching products and procedures are procedures in which bleaching takes place at a dental office. An advantage is that dentists are typically more capable of correctly applying the bleaching composition. A disadvantage is that visiting a dentist each time a person's desires whiter teeth is inconvenient. Therefore, in-office bleaching procedures typically utilize much stronger bleaching compositions able to bleach teeth to a desired whiteness in only one or a limited number of sessions. Such compositions, however, tend to be very caustic and irritating to soft oral tissues. Care must be to taken to isolate the teeth and protect surrounding gingival tissues.

In view of the foregoing, there is an ongoing need for improved bleaching methods that are easier to carry out and that reliably bleach a person's teeth while protecting surrounding soft oral tissues, as well as kits that facilitate such methods.

BRIEF SUMMARY OF THE PREFFERED EMBODIMENTS

The present invention relates to methods and kits for bleaching a person's teeth while protecting adjacent gingival tissue. The method involves applying a dental bleaching composition onto the surface of at least one tooth, applying a protective composition on or adjacent to gingival tissue, and placing a moisture-resistant barrier layer over the tooth surface(s) to be bleached. The barrier layer may, in some cases, optionally overlap the gingival margin to protect the protective composition. The protective composition forms a physical barrier that keeps the bleaching composition from contacting sensitive gingival tissue adjacent to tooth surfaces being bleached. The barrier layer protects at least the bleaching composition from saliva and/or mechanical forces and helps keep it from migrating into the oral cavity.

According to one embodiment, the dental bleaching composition is applied as a bead to a person's tooth surfaces, e.g., using a syringe, brush, or spatula. The protective composition may be applied to the gingival margin in the form of a bead, or it may be preloaded within a pre-formed dental treatment tray and applied to the gingival margin as the tray is placed over the teeth in a manner so as to overlap the gingival margin. When applied as a bead, the protective composition may be applied before, during or after applying the dental bleaching composition. When preloaded within a dental tray, the protective composition is typically applied to the gingival margin after the bleaching composition is applied. The moisture-resistant barrier layer is typically placed over the teeth after applying the dental bleaching composition to the tooth surface(s).

The dental bleaching composition used to bleach a person's teeth is a flowable bleaching gel composition that can be dispensed from a syringe or applied from a container using, e.g., a brush or spatula. Although the dental bleaching composition can have any desired viscosity and/or stickiness (ranging from runny to putty-like), it is preferably thick and sticky so as to act as a highly viscous glue or adhesive that helps reliably maintain both the bleaching composition and barrier layer against the person's tooth surfaces during the bleaching treatment. Exemplary dental bleaching compositions that may be used in the methods according to the invention comprise a dental bleaching agent, a liquid or gel solvent or carrier, a tissue adhesion agent, and other active agents, inert ingredients or adjuvents as desired.

The protective composition used to protect gingival tissue while bleaching a person's teeth may be applied as a bead onto the gingival margin, or it may be preloaded into a tray. It may comprise a hydrophilic gel composition that remains sticky and viscous throughout the bleaching procedure, or it may comprise a flexible polymerizable composition that is placed over the gingival tissue and then cured (e.g., by light or chemical initiated polymerization). In the case where the protective composition comprises a flexible polymerizable composition that is cured prior to placing a barrier layer over the teeth to be bleached, the outer surface of the protective composition may not be adhesive. In that case, a sticky and viscous dental bleaching composition is advantageously used in order to maintain the barrier layer over the person's teeth. The protective composition may include one or more active agents, inert components, and adjuvents as desired. In one embodiment, the protective composition may include a dental bleaching agent but in a lesser amount than the dental bleaching composition. Including a reduced quantity of bleaching agent results in a protective composition that is still gentler on soft tissues compared to the dental bleaching composition.

The barrier layer is advantageously formed from a moisture-resistant polymer material, examples of which include polyolefins, polyesters, ethylene-vinyl acetate copolymer (EVA), polyurethane, other polymers, and blends thereof. It may be in the form of a dental tray, sheet, strip, patch or other desired shape. The barrier layer is advantageously thin and flexible so as to conform to the shape of a person's teeth as a result of the adhesive nature of the protective composition and/or the dental bleaching composition. The barrier layer may be sufficiently sturdy as to assume a particular shape prior to use (e.g., a dental tray), or it may be so thin and flexible as to only be capable of maintaining a desired shape determined by an external support (e.g., an exoskeleton, such as an external support tray). In one embodiment, the barrier layer is reliably held in place over a user's teeth for a desired period of time by the adhesive action of the dental bleaching and/or protective composition.

According to one embodiment, the front surface of at least one tooth is bleached. According to another embodiment, both the front and lingual surfaces of at least one tooth are bleached. Bleaching both surfaces yields more esthetically appealing teeth and helps in bleaching the interproximal spaces between adjacent teeth when a plurality of teeth are bleached.

According to one embodiment, the dental bleaching methods are advantageously performed by a dental professional. In order to minimize the need for the patient to return for repeated bleaching sessions, the dental bleaching composition used to bleach the patient's teeth according to the inventive methods may advantageously include a relatively high concentration of dental bleaching agent (e.g., 35% carbamide peroxide for moderately quick bleaching, and 35% available hydrogen peroxide for extremely quick bleaching).

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 is a perspective view of a person's teeth and adjacent gingival tissue illustrating a bead of a dental bleaching composition being applied to the front surfaces of the teeth;

FIG. 2 is a perspective view of a person's teeth and adjacent gingival tissue illustrating a bead of a protective composition being applied to the gingival margin in order to provide a physical barrier between the bleaching composition on the person's tooth surfaces and adjacent gingival tissue;

FIG. 4 is a cross-sectional view of a tooth being bleached with a bleaching composition positioned on a surface of the tooth, a protective composition positioned at the gingival margin, and a barrier layer placed over the bleaching composition and protective composition;

FIG. 5A is a perspective view of a person's teeth and adjacent gingival tissue illustrating a bead of a protective composition that is a flexible polymerizable composition being applied to the gingival margin;

DETAILED DESCRIPTION OF THE PREFERRED EMBODIMENTS

I. Introduction and Definitions

Figure 3A:
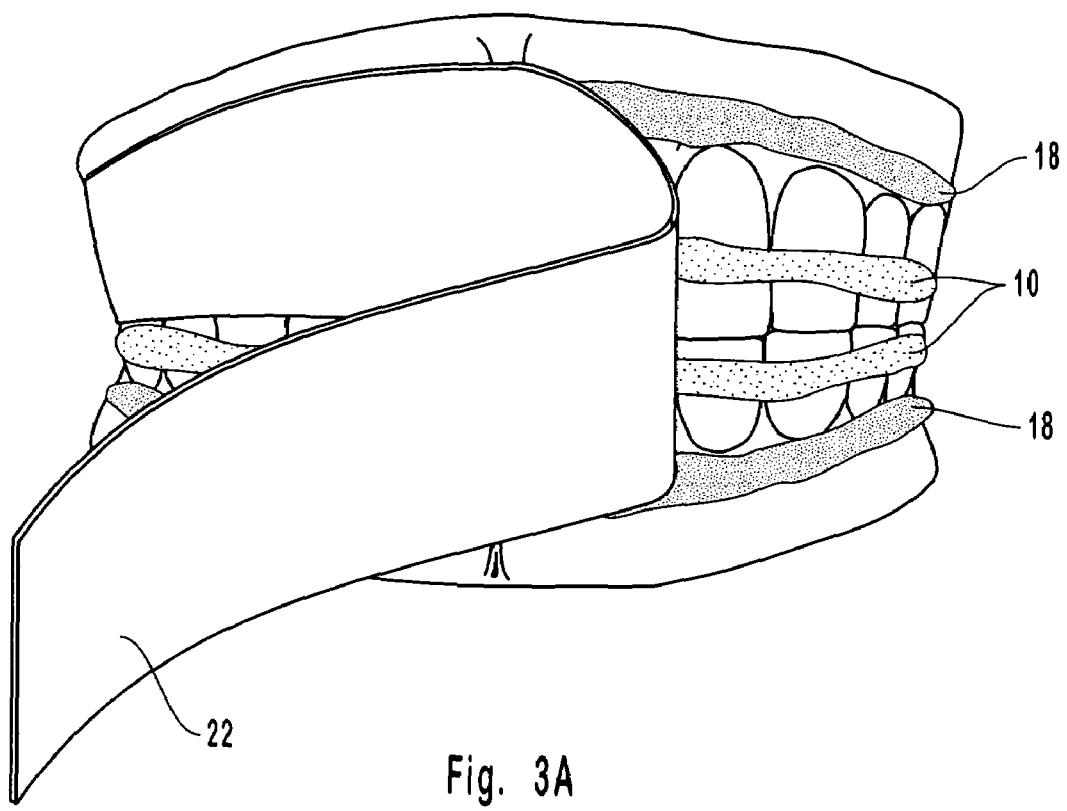
FIG. 3A is a perspective view of a person's teeth and adjacent gingival tissue with a moisture-resistant barrier layer initially in the form of a sheet, strip or patch being placed over the tooth surfaces and gingival margin.

The present invention relates to methods and kits for bleaching teeth while protecting gingival tissue from the bleaching composition. The inventive methods include applying a dental bleaching composition to at least one tooth surface, applying a protective composition on or adjacent to gingival tissue near the tooth surface, and placing a barrier layer over at least the bleaching composition to protect it from saliva and/or mechanical forces. The protective composition may be a sticky and viscous gel comprising a hydrophilic polymer as tissue adhesive agent, or it may comprise a flexible polymerizable composition.

The term "barrier layer", as used herein, refers to one or more layers of a material that protects at least the bleaching composition and, optionally, the protective composition from ambient moisture and saliva found within a person's mouth during the bleaching process and/or mechanical forces. The barrier layer may be in any desired form including, but not limited to, a dental tray, a tray-like shape, a strip or a patch. The terms "strip" and "patch" are essentially synonymous and refer to barrier layers and bleaching devices that are essentially flat or formless prior to placing the bleaching device over a person's teeth.

The term "gel" shall refer to bleaching and/or protective compositions that have been formulated or processed so as to be flowable, either by the force of gravity (i.e., having no yield stress) or that do not flow by the force of gravity but which are viscous or plastic such that they can be shaped or manipulated (e.g., they can be expressed from a syringe orifice or other dispensing means known in the art). The term "gel" broadly encompasses a wide range of compositions having greatly varying viscosities, although bleaching and protective gels according to the invention are preferably thick and viscous.

The term "dental tray", as used herein, refers to an appliance having a tray-like shape so as to facilitate placement of the tray over at least a portion of a person's dental arch. A "dental tray" or "tray-like" appliance includes a front side wall configured to engage front surfaces of a person's teeth when in use, a rear side wall extending laterally from the front side wall, either abruptly by one or more distinct angles or non-abruptly by a curved transition portion, configured to engage lingual surfaces of the person's teeth, and a trough between said front and rear side walls. A "dental tray" may be configured so that a portion of the front side wall, rear side wall, or a transition portion thereof (e.g., a bottom wall), engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°. In practice, the front and rear side walls will be offset by an angle that is preferably less than about 150°, more preferably less than about 120°, and most preferably less than about 90°.

The terms "strip" or "patch" are used interchangeably and shall refer to any barrier layer that is substantially flat, or that only has a slight curvature- or bend but that does not constitute a "dental tray", as that term is understood in the art. A "strip" or "patch", includes an inner surface or region generally oriented toward the front and/or rear surfaces of a person's teeth and/or gums when in use and an outer surface that is generally oriented away from the person's teeth and/or gums. A "strip" or "patch" may be configured so that a portion of the inner surface is oriented toward the incisal or occlusal edges of the person's teeth during use. The strip or patch may be curved or straight in one or both of the lengthwise and widthwise directions in order to fit over a user's teeth and/or gums in a desired manner.

The term "molecular weight", as used herein, shall refer to number average molecular weight expressed in Daltons, unless otherwise specified.

II. Dental Bleaching Methods

In order to bleach a person's teeth while protecting surrounding gingival tissues, the bleaching composition applied to one or more tooth surfaces is confined to the tooth surfaces and isolated from the gingival tissue by a protective composition that is applied on or adjacent to gingival tissue near the tooth surface(s) being bleached. A moisture-resistant barrier layer is placed over the teeth in order to protect the bleaching composition from ambient moisture and saliva found in the person's mouth, as well as mechanical forces that may be applied during the bleaching procedure (e.g., by the person's lips, cheeks and tongue). The barrier layer also serves to isolate the bleaching composition and keep it from diffusing into the oral cavity, further protecting soft gingival tissues found in the mouth.

The bleaching composition, protective composition and barrier layer may be applied or placed in any desired order, provided that the bleaching composition is applied to one or more tooth surfaces before the barrier layer is placed over at least the one or more teeth being bleached. Reference is now made to the drawings, which depict exemplary methods for bleaching a person's teeth while protecting gingival tissue.

FIG. 1 illustrates a person's teeth being coated with a dental bleaching composition according to one embodiment of the invention. More particularly, a bead of a dental bleaching composition 10 is shown being applied to the front (or labial) surfaces of a person's teeth 12 using a syringe 14. It will be appreciated that one or both of the labial and lingual surfaces of a tooth may be bleached. Any syringe known in the art can be used to apply the bleaching composition 10. Examples include syringes used to load bleaching gel into custom or non-custom trays, syringes without syringe tips, and syringes with syringe tips (e.g., with or without a brush tip). Alternatively, any other applicator known in the art (e.g., brushes or spatulas) can be used to apply the bleaching composition 10 to the tooth surfaces. When applying the bleaching composition 10, care should be taken to avoid applying the bleaching composition to the gingiva 16, particularly when using a bleaching composition that includes a relatively high concentration of bleaching agent.

FIG. 2 shows a bead of a protective composition 18 being applied to the gingival margin 20, which is located at the interface between the exposed surfaces of the teeth 12 and the gingiva 16. One or both of the labial and lingual aspects of the gingival margin 20 can be coated with the protective composition 18 depending on whether one or both surfaces of the teeth 12 are being bleached. The protective composition 18 is also shown being applied using a syringe 14. It will be appreciated that any applicator known in the art can be used to apply the protective composition 18. It will also be appreciated that the protective composition 18 can be applied to the gingival margin 20 either before, during or after the dental bleaching composition 10 is applied to the teeth 12. A double barreled syringe (not shown) can be employed if it is desired to apply the protective composition 18 and bleaching composition 10 at the same time.

FIG. 3A shows a barrier layer 22, which is initially in the form of a sheet, strip or patch, being placed over the teeth 12 in order to protect the dental bleaching composition 10 from ambient moisture or saliva found in the person's mouth, as well as mechanical forces that may dislodge the bleaching composition 10 from its intended location. In the case where the protective composition 18 is a hydrophilic gel that requires no polymerization, it may be advantageous for the barrier layer 22 to extend over the gingival margin 20 in order to also protect the protective composition 18 from ambient moisture or saliva found in the person's mouth, as well as mechanical forces that may dislodge the protective composition 18 from its desired location. In the case where the protective composition 18 is a flexible polymerizable composition, it may be desirable to cure the composition (e.g., by chemical or photo initiated polymerization) before placing the barrier layer 22 over the person's teeth (See FIGS. 5A and 5B).

Figure 3B:
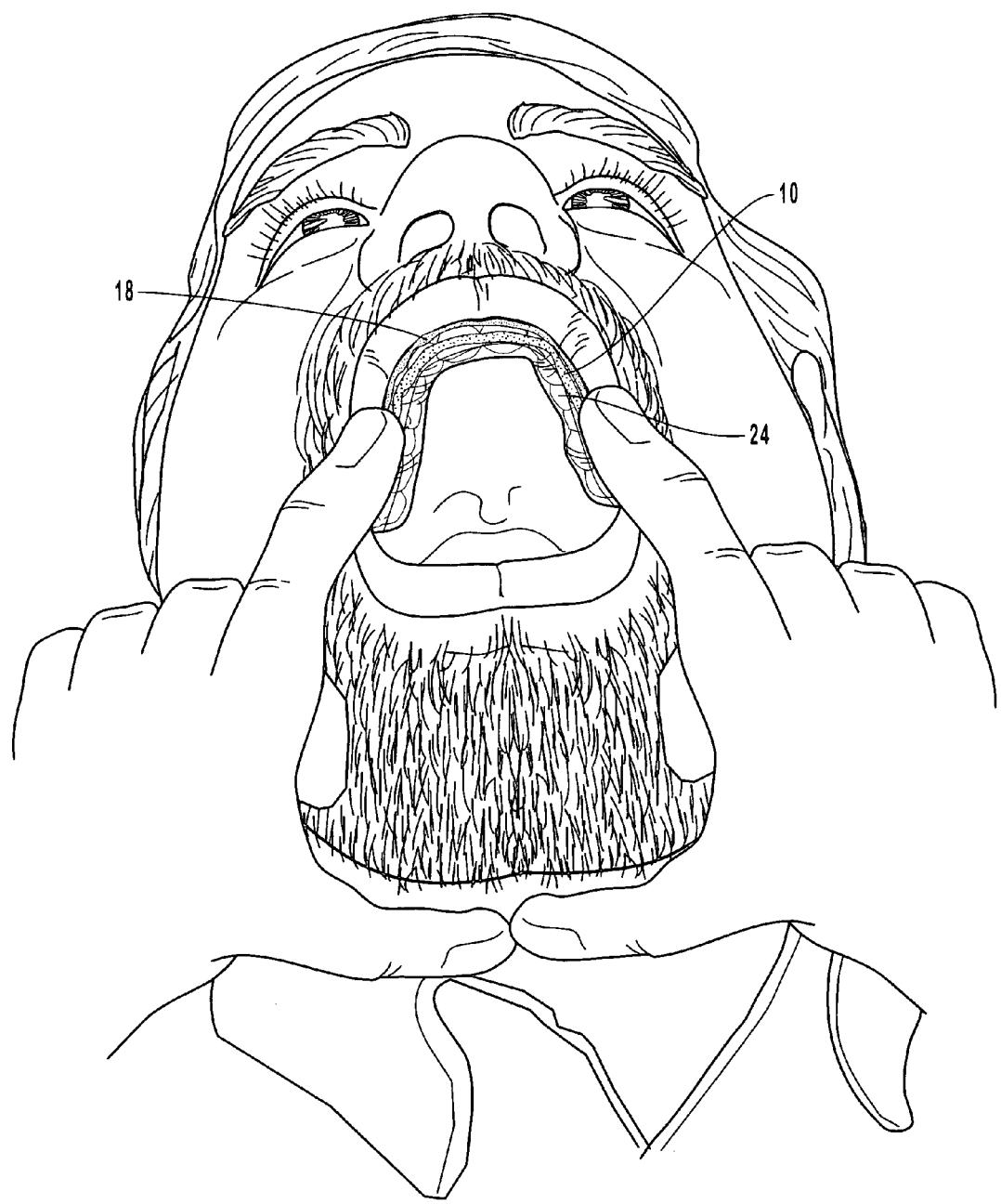
FIG. 3B is a perspective view of a person's teeth and adjacent gingival tissue with a moisture-resistant barrier layer in the form of a dental tray being placed over the tooth surfaces and gingival margin.

FIG. 3B alternatively shows a barrier layer in the form of a dental tray 24 being placed over the teeth 12 in order to protect the dental bleaching composition 10 from ambient moisture or saliva found in the person's mouth, as well as mechanical forces that may dislodge the bleaching composition 10 from its intended location. In the case where the protective composition 18 is a hydrophilic gel that requires no polymerization, it may be advantageous for the dental tray 24 to extend over the gingival margin 20 (see FIG. 3A) in order to also protect the protective composition 18 from ambient moisture or saliva found in the person's mouth, as well as mechanical forces that may dislodge the protective composition 18 from its desired location. In the case where the protective composition 18 is a flexible polymerizable composition, it may be desirable to cure the composition (e.g., by chemical or photo initiated polymerization) before placing the dental tray 24 over the person's teeth.

FIG. 4 is a cross-sectional view showing a dental bleaching composition 10 applied to both the labial and lingual surfaces of the tooth 12, a protective composition 18 applied to both the labial and lingual aspects of the gingival margin 20, and a barrier layer 22 over the tooth 12 so as to cover and protect both the bleaching composition 10 and protective composition 18. The barrier layer 22 may, of course, have any desired shape or configuration prior to being placed over the tooth, including being a, sheet, strip, patch, or dental tray 24.

FIG. 5A alternatively shows a protective composition 30 that is a flexible polymerizable composition being applied over gingival tissue 32 adjacent to teeth 34 to be bleached. Because the protective composition 30, when cured, will not wash away or be disrupted by saliva found in the person's mouth, or dislodge as a result of mechanical forces that may be caused by the person's lips, cheeks or tongue, it is not necessary to cover it with a barrier layer during the bleaching procedure. As a result, the flexible polymerizable composition 30 may optionally be applied so as to cover more of the gingival tissue, if desired, than hydrophilic gels that are more easily washed away or dislodged. FIG. 5A, for example, shows the flexible polymerizable composition 30 being applied to gingival tissue well beyond the gingival margin 36.

Figure 5B:
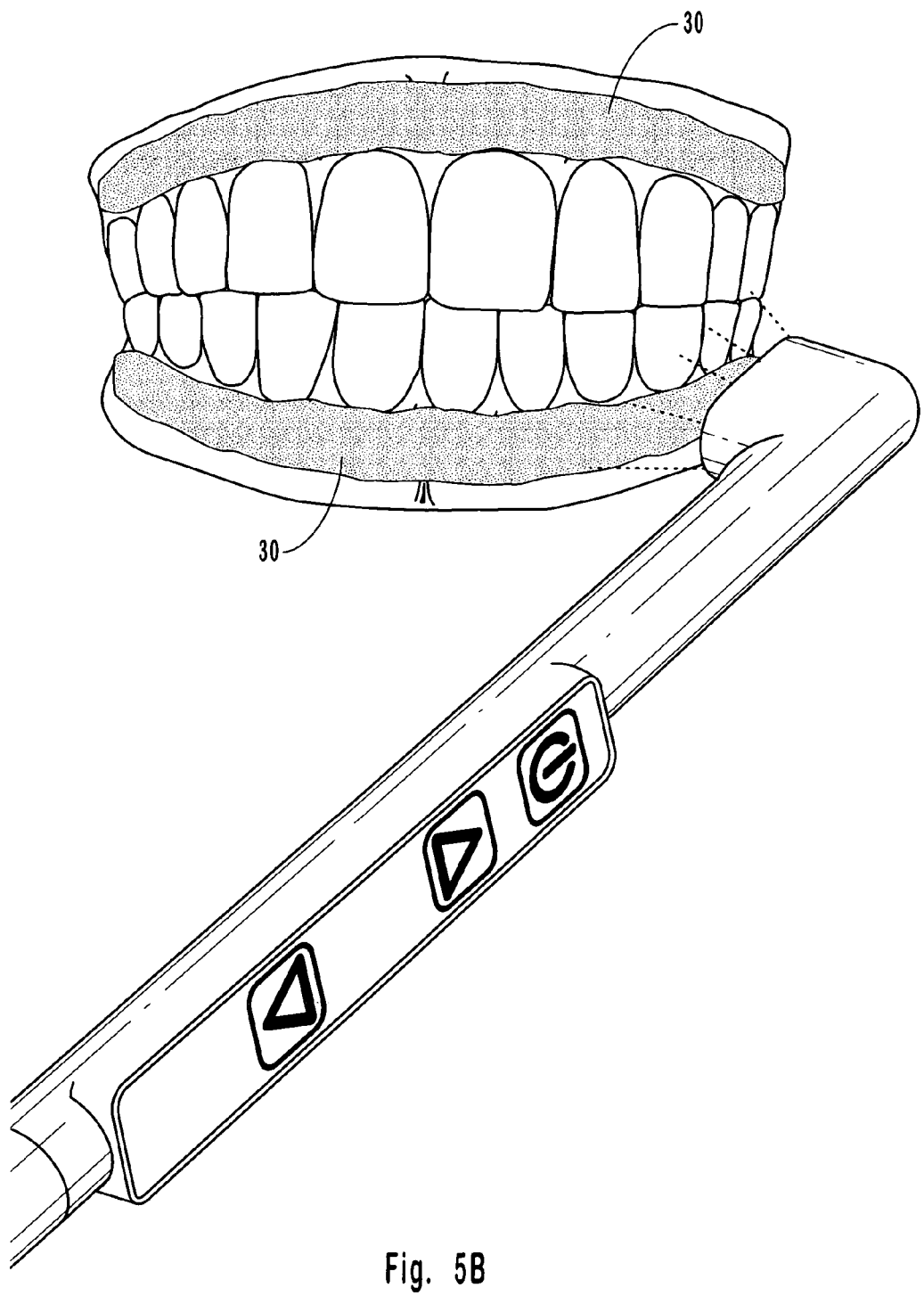
FIG. 5B shows the flexible polymerizable composition of FIG. 4 being light cured.

FIG. 5B shows the flexible polymerizable composition 30 being light cured using a standard dental curing light. It will be appreciated that the flexible polymerizable composition 30 may alternatively be formulated so as to be chemical cured (e.g., as a two-part composition that is mixed just prior to use). In that case, light curing would be unnecessary.

Figure 6A:
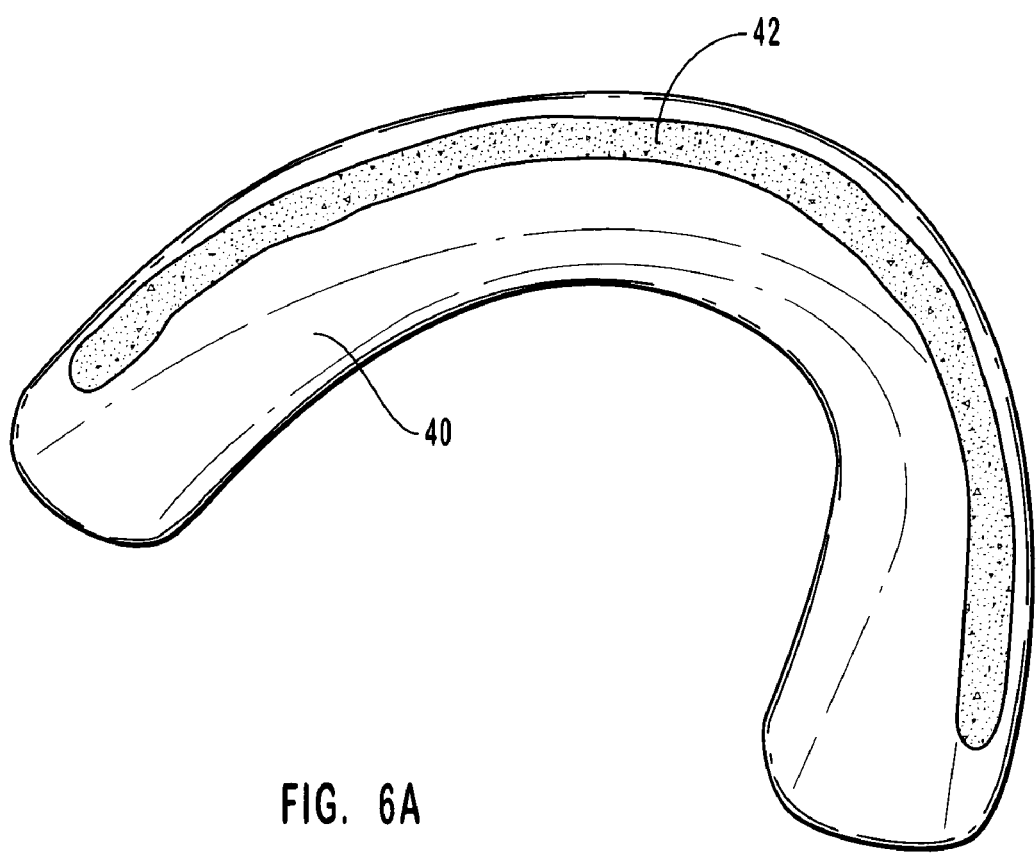
FIG. 6A illustrates a protective composition preloaded within a dental tray prior to placing the tray over the person's teeth.
Figure 6B:
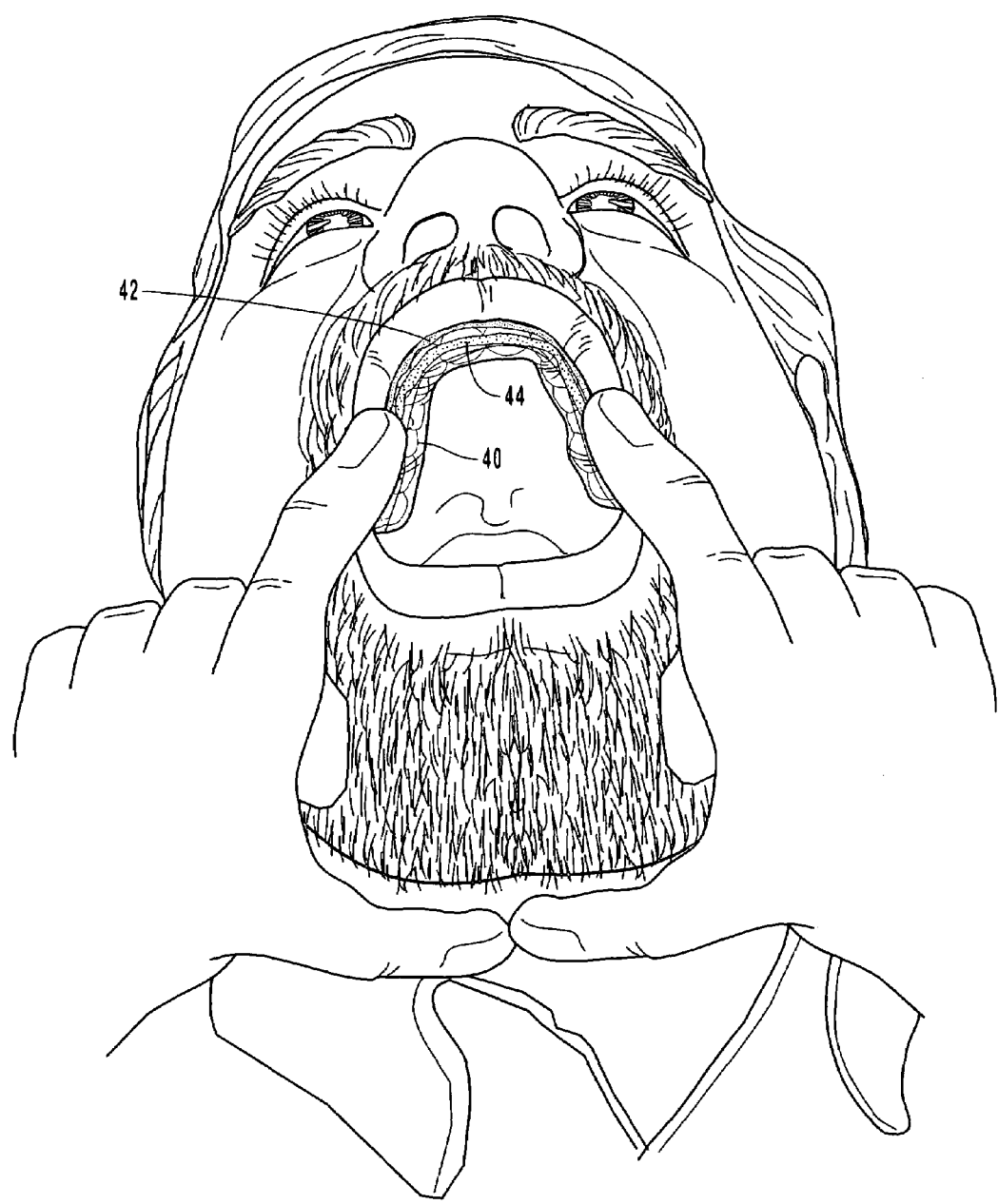
FIG. 6B shows the dental tray preloaded with a protective composition of FIG. 6A being placed over a person's teeth.

FIGS. 6A and 6B depict an alternative method of applying a protective composition to a person's gingival tissue (e.g., the gingival margin). More particularly, FIG. 6A shows a barrier layer in the form of a dental tray 40 into which a protective composition 42 has been loaded. The protective composition 42 may be loaded into the dental tray 40 by the dental practitioner prior to performing the bleaching method. Alternatively, the protective composition 42 may be preloaded into the dental tray 40 by the manufacturer. The protective composition 42 is placed in a position so that, when the dental tray 40 is placed over a person's teeth, the protective composition 42 will be located at or near the gingival margin.

FIG. 6B shows the dental tray 40 loaded with the protective composition 42 being placed over a person's teeth. In this case, a dental bleaching composition 44 is advantageously placed over the person's tooth surfaces prior to placing the dental tray 40 over the teeth. The protective composition 42 is able to protect the gingival tissue surrounding the teeth in substantially the same way as protective compositions applied prior to placing a barrier layer over the teeth.

Figure 7:
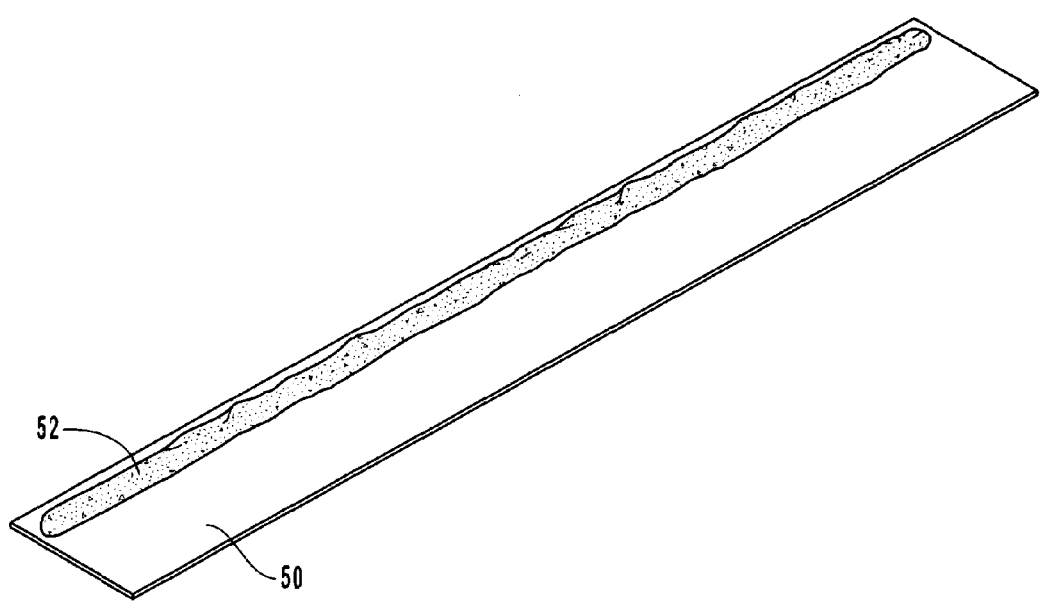
FIG. 7 illustrates a protective composition pre-applied to a sheet, strip or patch barrier layer prior to placing the barrier layer over the person's teeth.

FIG. 7 alternatively shows a barrier layer 50 in the form of a sheet, strip or patch onto which a protective composition 52 has been placed. The protective composition 52 may be placed onto the barrier layer 50 by the dental practitioner prior to performing the bleaching method. Alternatively, the protective composition 52 may be pre-placed onto the barrier layer 50 by the manufacturer. The protective composition 52 is placed in a position so that, when the barrier layer 50 is placed over a person's teeth, the protective composition 52 will be located at or near the gingival margin.

III. Dental Bleaching Kits

For convenience of use, a dental bleaching composition, a protective composition, and a barrier layer (e.g., sheet, strip, patch or dental tray) may be packaged together and sold as a kit. It is within the scope of the invention to provide bleaching compositions, protective compositions, and barrier layers that are initially separate and that are brought together by the end user (e.g., a dental practitioner). For example, the dental bleaching composition and protective composition may be packaged within a syringe for storage and ease of delivery. In the case where they are to be applied in succession, they may each be separately packaged in a respective syringe. In the case where they are to be applied simultaneously, they may be packaged in a double barreled syringe, with the barrel ends being spaced apart so that the bleaching composition can be applied onto a person's tooth surfaces while simultaneously applying the protective composition onto the gingival margin.

Alternatively, the protective composition may be provided to the use already applied to the barrier layer. For example, the protective composition may be preloaded within a dental tray or placed onto a sheet, strip or patch by the manufacturer. The dental bleaching composition is advantageously loaded within a syringe for separate delivery.

In order to facilitate placement of a dental tray over a person's teeth (with or without a protective composition preloaded therein), the dental tray may be installed using an exoskeleton support tray. Examples of thin, flexible dental trays that can be used in combination with an exoskeleton tray in order to deliver a dental composition onto a person's teeth and/or gums are disclosed in U.S. application Ser. No. 10/444,242, filed May 23, 2003; U.S. application Ser. No. 10/783,597, filed Feb. 19, 2004; and U.S. application Ser. No. 10/783,750, filed Feb. 19, 2004.

IV. Exemplary Compositions and Materials for Use with Bleaching Methods and Kits The bleaching methods and kits according to the invention can be carried out or prepared using any dental bleaching composition, protective composition, and barrier layers or materials known in the art. The following are given by way of example only, not by limitation.

A. Dental Bleaching Compositions

Dental bleaching compositions for use in the bleaching methods and kits of the invention may comprise any bleaching composition known in the art. They may comprise a sticky or non-sticky gel. Preferred bleaching compositions are substantially viscous and tacky in order to at least partially help in retaining the barrier layer against a person's teeth during tooth bleaching. In general, dental bleaching compositions will include at least one dental bleaching agent and a liquid or gel, solvent, carrier or vehicle into which the dental bleaching agent is dispersed. In a preferred embodiment, the bleaching compositions will also include at least one tissue adhesion (or thickening) agent. The bleaching gel may optionally include other active agents (e.g., desensitizing agents, remineralizing agents, antimicrobial agents, and the like), as well as inert ingredients (e.g., plasticizers, humectants, neutralizing agents, thickening agents, flavorants, sweeteners, and the like).

Exemplary dental bleaching compositions and methods for making such compositions are disclosed in U.S. Pat. No. 5,376,006; U.S. Pat. No. 5,785,527; U.S. Pat. No. 5,851,512; U.S. Pat. No. 5,858,332; U.S. Pat. No. 5,985,249; U.S. Pat. No. 6,306,370; U.S. Pat. No. 6,309,625; U.S. Pat. No. 6,312,671; U.S. Pat. No. 6,322,774; U.S. Pat. No. 6,368,576; U.S. Pat. No. 6,387,353; U.S. Pat. No. 6,500,408; and U.S. Pat. No. 6,503,485. For purposes of disclosing dental bleaching compositions and methods of making such compositions, the foregoing patents are incorporated herein by reference.

Following are exemplary bleaching agents, solvents or carriers, tissue adhesion agents, and other components within exemplary bleaching compositions that may be used to bleach teeth according to the invention.

1. Bleaching Agents

Any bleaching agent capable of bleaching teeth can be used. A common dental bleaching agent that is known to bleach teeth and that has been found to be safe for oral use is hydrogen peroxide. However, hydrogen peroxide does not itself exist free in nature, but as an aqueous solution or a complex. Aqueous hydrogen peroxide is an acceptable dental bleaching agent to the extent that an anhydrous bleaching composition is not desired. Non-limiting examples of hydrogen peroxide complexes include carbamide peroxide and metal perborates (e.g., sodium perborate). Other bleaching agents that can be used to bleach teeth include, but are not limited to, metal percarbonates (e.g., sodium percarbonate), metal peroxides (e.g., calcium peroxide), metal chlorites and hypochlorites, peroxy acids (e.g., peroxyacetic acid), and peroxy acid salts.

Bleaching agents within the dental bleaching compositions according to the invention can have any desired concentration, e.g., between 1-90% by weight of the dental bleaching composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period. For in-office bleaching procedures, the one or more bleaching agents will preferably be included in an amount greater than about 10% by weight of the dental bleaching composition, more preferably greater than about 20% by weight, and most preferably greater than about 30% by weight.

2. Carriers and Vehicles

Dental bleaching compositions will typically include one or more liquid or gel, solvents, carriers or vehicles into which the dental bleaching agent and other components are dissolved or dispersed. The solvent, carrier or vehicle will typically comprise the balance of components in the dental bleaching gel in addition to the bleaching agent, optional tissue adhesion agent, and other components. Examples of liquid or gel solvents, carriers or vehicles include, but are not limited to, water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

3. Tissue Adhesion Agents

Useful tissue adhesion agents (or tackifying agents), which can also act as thickening agents that increase the viscosity of the dental bleaching composition, include a wide variety of hydrophilic polymers. Examples of hydrophilic polymer tissue adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like.

Non-limiting examples of polyvinyl pyrrolidone polymers that have been used in formulating dental bleaching compositions according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the dental bleaching composition is a sticky and viscous gel, the one or more tissue adhesion agents are preferably included in an amount in a range of about 1% to about 50% by weight of the dental bleaching composition, more preferably in a range of about 3% to about 30% by weight, and most preferably in a range of about 5% to about 20% by weight.

4. Other Components

The dental bleaching compositions may optionally include other active or inert components as desired to yield bleaching compositions having desired properties. Examples include bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal pyrophosphates, alkyl sulfates, such as sodium lauryl sulfate, tin salts, such as sodium stannate, and tartrates), neutralizing agents (e.g., sodium hydroxide and triethanolamine), inorganic thickening agents (e.g., fumed silica), desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

B. Protective Compositions

Protective adhesive compositions used in bleaching methods and kits according to the invention are characterized as having no bleaching agent, or significantly less bleaching agent, than the dental bleaching composition. Aside from that, they may include any of the components set forth above with respect to the dental bleaching composition. The protective composition is positioned relative to the bleaching composition so as to shield a person's gums or periodontal tissue from the bleaching composition during use, thereby confining the bleaching agent within the bleaching composition to an area adjacent to the person's tooth surfaces to be bleached.

One example of a protective composition is a flexible polymerizable material. Another example is a sticky and viscous hydrophilic gel. Examples of flexible polymerizable materials are disclosed in U.S. Pat. No. 6,048,202, U.S. Pat. No. 6,086,370 and U.S. Pat. No. 6,305,936. For purposes of disclosing protective compositions, the foregoing patents are incorporated herein by reference. Examples of adhesive hydrophilic gel compositions that can be used as a protective composition within the scope of the invention are disclosed in U.S. Pat. No. 5,770,182; U.S. Pat. No. 5,855,870; U.S. Pat. No. 5,851,512; U.S. Pat. No. 5,985,249; and U.S. Pat. No. 6,036,943. For purposes of disclosing protective compositions, the foregoing patents are incorporated herein by reference.

In general, protective compositions that are hydrophilic gels will include at least one tissue adhesion (or tackifying) agent and a liquid or gel solvent, carrier or vehicle into which the tissue adhesion agent is dispersed. The tissue adhesion agent preferably comprises a hydrophilic polymer (e.g., one or more of the hydrophilic polymers discussed above with respect to the dental bleaching composition). The solvent, carrier or vehicle may comprise any of the solvents, carriers or vehicles discussed above with respect to the bleaching composition.

In one embodiment, the protective composition may include a dental bleaching agent in a lesser amount than the dental bleaching composition. In that way, the portion of the tooth, if any, that contacts the protective composition rather than the bleaching composition can still be subjected to tooth bleaching. In addition, peroxide bleaching agents are known to have an antimicrobial effect, thus potentially acting as a disinfecting and freshening agent to gums and periodontal tissue when included in an amount that does not cause damage to or burn such tissues. The protective compositions may include a dental bleaching agent in a range of 0% to about 10% by weight of the adhesive composition, preferably in a range of about 1% to about 10%, and more preferably in a range of about 5% to about 10% by weight.

The protective composition may include other components as desired, including colorants (e.g., carotene), gingival soothing agents (e.g., aloe vera, mild potassium nitrate, isotonic solution-forming salts (e.g., sodium chloride in an amount of about 0.9% by weight), and anesthetics (e.g., benzocaine, lidocain and the like), antioxidants (e.g., vitamin A, vitamin C, vitamin E, other vitamins, chlorophyll and carotene), flavoring agents, antimicrobial agents and preservatives (e.g., sodium benzoate, parabens, triclosan, phenols, chlorhexidine, and cetylpyridinium chloride), mouth freshening agents (e.g., camphor and wintergreen), inorganic thickening agents (e.g., fumed silica and fumed aluminum oxide), remineralizing agents (e.g., sodium fluoride or other fluoride salts), bleaching agent stabilizers, antiplaque agents, anti-tartar agents, and other adjuvents as desired.

At least a portion of the protective composition may also include one or more bleaching agent activators that are released when moistened with saliva and/or mixed with the dental bleaching composition during a bleaching procedure. The protective composition may comprise any known bleaching agent activator that is capable of destabilizing a dental bleaching agent in order to accelerate bleaching. When peroxides are destabilized they more rapidly release oxygen radicals, which cause tooth bleaching.

One class of bleaching agent activators includes bases (i.e., substances that raise the pH in aqueous systems). Examples of useful bases that can destabilize bleaching agents and thereby accelerate bleaching include oxides, hydroxides, carbonates, and bicarbonates of alkali metals and alkaline earth metals, and amines. Non-limiting examples include sodium oxide, sodium hydroxide, potassium oxide, potassium hydroxide, sodium carbonate, sodium bicarbonate, ammonium hydroxide, magnesium hydroxide, sodium phosphate tribasic, and ethanolamine. Bases, when used as bleaching agent activators, are preferably included in an amount in a range of about 0.1% to about 20% by weight of the protective composition, more preferably in a range of about 1% to about 10% by weight, and most preferably about 7% by weight.

Another class of bleaching agent activators includes metals and metal compounds. Examples of metals and metal compounds include transition metals (e.g., powders or fine particulates of iron, cobalt, nickel, copper, zinc, manganese, chromium, and the like) or metal compounds (e.g., halides or sulfates of iron, cobalt, nickel, copper, zinc, manganese, chromium, and the like). More specific examples include iron and manganese metal, manganese chloride, manganese citrate, ferrous sulfate, and manganese sulfate.

Another class of bleaching agent activator includes enzymes, particularly organo-metallic enzymes containing transition metals, such as iron. One example is "catalase", which is described more particularly in U.S. Pat. No. 6,485,709 to Baneijee et al.

Metals, metal compounds, and organo-metallic enzymes, when used as a bleaching agent activator, are preferably included in an amount in a range of about 0.01% to about 20% by weight of the protective composition, more preferably in a range of about 0.05% to about 10% by weight, and most preferably in a range of about 0.1% to about 5% by weight.

C. Barrier Layers

The barrier layer used in the inventive methods and kits can have any desired shape or thickness. It is preferably moisture-resistant in order to protect at least the bleaching composition, and optionally the protective composition, from ambient moisture or saliva found in a person's mouth, as well as mechanical forces (e.g., from the person's lips, cheeks or tongue). According to one embodiment, the barrier layer comprises a thin, flexible membrane formed from a moisture-resistant polymer material. The barrier layer may comprise a conventional dental tray, examples of which include both customized and non-custom dental trays, or it may initially be a sheet, strip or patch, or it may have some other configuration.

Examples of materials that can be used to form the barrier layer include, but are not limited to, polyolefins, wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Examples of suitable polyolefins that can be uses to make the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The barrier layer may comprise a polymeric blend and/or multiple layers comprising two or more of the foregoing materials. Plasticizers, flow additives, and fillers known in the art can be used as desired to modify the properties of any of the foregoing polymers used to form the barrier layer.

According to one embodiment, the barrier layer is formed of a mixture of ethylene-vinyl acetate copolymer (EVA) and polypropylene (PP), e.g., about 20% PP, with the balance comprising ethylene-vinyl acetate (EVA) and optionally other polymers and/or small quantities of additives such as plasticizers.

Other materials that can act as a barrier layer include cellulosic ethers, cellulose acetate, polyvinyl acetate, polyvinyl alcohol, shellac, and chemical or light-cure materials (e.g., methacrylate or acrylate resins). Examples of useful cellulosic ethers that can be used to form a barrier layer include, but are not limited to, ethyl cellulose, propyl cellulose, isopropyl cellulose, butyl cellulose, t-butyl cellulose, and the like.

In general, the thickness of the barrier layer can be selected to yield a dental bleaching device having a desired level of strength, rigidity, resilience, and flexibility. In order for the barrier layer to be sufficiently flexible so as to conform to a person's teeth as result of adhesive action by the bleaching composition and/or protective adhesive composition, the barrier layer will preferably have a thickness ranging from about 0.025 mm to about 1.5 mm, more preferably in a range of about 0.05 mm to about 1 mm, and most preferably in a range of about 0.1 mm to about 0.75 mm.

D. EXAMPLES

The following are several examples of dental bleaching compositions that can used to bleach a person's teeth and protective compositions that can be used to protect soft gingival tissues from the bleaching composition. Unless otherwise indicated, all percentages are by weight.

Example 1

A dental bleaching composition suitable for use in bleaching a person's teeth was formed by mixing together the following components:

| | |
|---|---|
| Water | 22.5% |
| EDTA | 0.1% |
| Carbamide Peroxide | 18.5% |
| Sucralose (25% in water) | 0.75% |
| Glycerin | 41.6% |
| CARBOPOL 974 | 5.3% |

-continued

| | |
|---|---|
| NaOH (50% in water) | 2.25% |
| Polyvinyl Pyrrolidone (M.W. > 1 million) | 2% |
| Carboxy Methyl Cellulose | 4% |
| Flavor (peach, watermelon or peppermint) | 3% |

In addition, a protective composition suitable for protecting a person's soft gingival tissue from the bleaching composition was formed by mixing together the following components:

| | |
|---|---|
| Ethanol | 31.95% |
| Water | 10% |
| Polyvinyl pyrrolidone (M.W. > 1 million) | 27% |
| Polyvinyl pyrrolidone (M.W. ≈ 60,000) | 10% |
| Sodium Lauryl Sulfate | 0.5% |
| Glycerin | 15% |
| Sucralose (25% solution) | 0.5% |
| Peach Flavor | 4% |
| Potassium Nitrate | 0.8% |
| Sodium Fluoride | 0.25% |

The dental bleaching composition and protective composition were preloaded into a thin, flexible dental tray comprising a moisture-resistant blend of EVA and polypropylene. The bleaching composition was located in the middle of the trough and the protective composition was located near the rim of the front wall of the tray. The dental tray with the bleaching and protective compositions preloaded therein was placed over the person's teeth and so as to overlap the gingival margin. In this way, the dental bleaching composition was applied to the person's tooth surfaces and the protective composition was applied to the gingival margin adjacent to the tooth surfaces at substantially the same time. The dental tray shielded the bleaching composition and protective composition from saliva found in the person's mouth. It also protected them from mechanical forces (e.g., from the person's lips and tongue) that might have otherwise disrupted or removed the bleaching composition and protective composition from their designated locations on the person's tooth surfaces and gingival margin, respectively. The bleaching composition caused noticeable bleaching of the person's teeth, while the protective composition helped prevent the adjacent gingival tissue from being irritated by the bleaching agent within the bleaching composition.

Example 2

Alternatively, the flexible dental tray was nested within an exoskeleton tray having a handle, which helped in placing the dental tray over the person's teeth. The exoskeleton tray was more rigid and helped maintain the thin, flexible dental tray in the shape of a tray as it was placed over the person's teeth.

Example 3

Alternatively, a barrier layer comprising a flexible sheet of a moisture-resistant material is adapted to the person's teeth and held in place in the form of a tray-like barrier during the bleaching treatment by the adhesive action of the protective composition and the dental bleaching composition of Example 1. The sheet protects the bleaching and protective compositions from saliva and/or mechanical forces. The dental bleaching composition and/or the protective composition of Example 1 may be placed onto the sheet prior to placing the sheet over the person's teeth and gingival margin, or one or both may be applied directly to the person's teeth and/or gingival margin, respectively, prior to placing the flexible barrier sheet.

Example 4

Alternatively, the protective composition of Example 1 is first applied to the gingival margin as a bead. Then, the dental bleaching composition of Example 1 is applied to a person's tooth surfaces as a bead. Thereafter, a moisture-resistant barrier layer comprising a tray or sheet is placed over the person's teeth and gingival margin to protect the bleaching and protective compositions from saliva and/or mechanical forces.

Example 5

Alternatively, the dental bleaching composition of Example 1 is applied to the person's teeth as a bead over the person's teeth following by applying a dental tray into which the protective composition of Example 1 is preloaded in order for the protective composition to be applied to the person's gingival margin.

Example 6

Alterntively, a flexible polymerizable material, such as OPALDAM, a proprietary barrier material available from Ultradent Products, Inc., South Jordan, Utah, is placed over the gingival margin instead of the protective composition of Example 1 and cured (e.g., by light or chemical initiated polymerization). The dental bleaching composition of Example 1 is applied to the person's teeth according to any of Examples 1-5, and the flexible polymerizable material protects gingival tissue from the bleaching composition.

Example 7

A dental bleaching composition suitable for use in bleaching a person's teeth was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 (SiO$_2$) | 7% |
| Peach Flavor | 2% |
| Polyethylene Glycol (M.W. = 20,000) | 20% |

The bleaching composition is used to bleach a person's teeth according to the method described in any of Examples 1-6.

Example 8

A dental bleaching composition suitable for use in bleaching a person's teeth was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

The bleaching composition is used to bleach a person's teeth according to the method described in any of Examples 1-6.

Example 9

A dental bleaching composition suitable for use in bleaching a person's teeth was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

The bleaching composition is used to bleach a person's teeth according to the method described in any of Examples 1-6.

Example 10

A dental bleaching composition suitable for use in bleaching a person's teeth was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

The bleaching composition is used to bleach a person's teeth according to the method described in any of Examples 1-6.

Example 11

A dental bleaching composition suitable for use in bleaching a person's teeth was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

The bleaching composition is used to bleach a person's teeth according to the method described in any of Examples 1-6.

Example 12

A dental bleaching composition suitable for use in bleaching a person's teeth was formed by mixing together the following components:

| | |
|---|---|
| Water | 22.5% |
| EDTA | 0.1% |
| Carbamide Peroxide | 18.5% |
| Sucralose (25% in water) | 0.75% |
| Glycerin | 41.6% |
| CARBOPOL 974 | 5.3% |
| NaOH (50% in water) | 2.25% |
| Polyvinyl Pyrrolidone (M.W. > 1 million) | 2% |
| Carboxy Methyl Cellulose | 4% |
| Flavor (peach, watermelon or peppermint) | 3% |

The bleaching composition is used to bleach a person's teeth according to the method described in any of Examples 1-6.

Example 13

OPALESCENCE QUICK, a proprietary dental bleaching composition available from Ultradent Products, Inc., South Jordan, Utah, containing 35% by weight carbamide peroxide, is used to bleach a person's teeth according to the method described in any of Examples 1-6.

Example 14

OPALESCENCE EXTRA, a proprietary one-part dental bleaching composition available from Ultradent Products, Inc., South Jordan, Utah, containing 35% by volume available hydrogen peroxide, is used to bleach a person's teeth according to the method described in any of Examples 1-6.

Example 15

OPALESCENCE EXTRA BOOST, a proprietary two-part dental bleaching composition available from Ultradent Products, Inc., South Jordan, Utah, containing 35% by volume available hydrogen peroxide, is used to bleach a person's teeth according to the method described in any of Examples 1-6.

Example 16

The protective composition of Example 1 is modified by adding a dental bleaching agent (e.g., carbamide peroxide) in an amount that is less than the amount of bleaching agent within the dental bleaching composition of Example 1, more specifically, in amounts of 2%, 4%, 6%, 8% and 10%, respectively. The protective composition modified by adding a bleaching agent is able to bleach the tooth surface at the gingival margin and/or "freshen" the gingival tissue by, e.g., killing bacteria that may otherwise cause irritation or bad breath. Because the bleaching agent in the protective adhesive composition has a concentration that is lower than the concentration of bleaching agent in the bleaching composition, the protective composition causes significantly reduced irritation of the gingival tissue compared to the bleaching composition.

Example 17

The dental bleaching compositions in any of the foregoing examples are modified by adding one or more of a desensitizing agent, remineralizing agent, antimicrobial agent, antiplaque agent, anti-tartar gent, or other medicament.

Example 18

The protective composition of Examples 1 and 16 are modified by adding one or more of a colorant, gingival soothing agent, isotonic solution-forming salt, anesthetic, antioxidant, flavoring agent, preservative, mouth freshening agent, detergent, inorganic thickening agent, remineralizing agent, antiplaque agent, anti-tartar agent, freshening agent, or antioxidant.

Example 19

The protective compositions of Examples 1, 16 and 18 are modified by adding an effective amount of one or more bleaching agent activators (e.g., 5% of a an alkali metal or alkaline earth metal base and/or 1% of a metal, metal compound or organo-metallic enzyme).

Example 20

Bleaching is enhanced according to any of the foregoing examples by irradiating the bleaching composition with light (e.g., from a dental curing light or laser) in order to further accelerate bleaching of the person's teeth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of bleaching at least one of a person's teeth, comprising:
  prior to applying a moisture-resistant barrier layer, applying a dental bleaching composition onto at least one tooth surface, wherein said bleaching composition comprises at least one bleaching agent and a carrier for said bleaching agent;
  applying a protective composition on or adjacent to gingival tissue in order to form a barrier between the gingival tissue and said bleaching composition, and wherein the protective composition includes
    at least one tissue adhesion agent that includes at least one hydrophilic polymer, and a dental bleaching agent in a lower concentration than the dental bleaching agent contained in said dental bleaching composition;

placing a moisture-resistant barrier layer over the tooth surface in order to protect said bleaching composition from saliva and/or mechanical forces; and bleaching the tooth surface by means of said bleaching composition while protecting the gingival tissue near the tooth surface by means of said protective composition.

2. A method as defined in claim 1, said dental bleaching composition being applied over the at least one tooth using a syringe.

3. A method as defined in claim 1, said dental bleaching composition being applied to a plurality of tooth surfaces.

4. A method as defined in claim 1, wherein said dental bleaching composition is applied to labial and lingual surfaces of at least one tooth.

5. A method as defined in claim 1, wherein said dental bleaching composition is a sticky and viscous gel that contributes to holding said barrier layer over said tooth.

6. A method as defined in claim 1, wherein said dental bleaching composition further comprises at least one tissue adhesion agent selected from the group comprising polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

7. A method as defined in claim 1, wherein said dental bleaching composition further comprises at least one member selected from the group comprising dental desensitizing agents, stabilizing agents, remineralizing agent, antimicrobial agents, antiplaque agents, and anti-tartar agents.

8. A method as defined in claim 1, wherein said protective composition is applied prior to placing said barrier layer.

9. A method as defined in claim 8, wherein said protective composition is applied prior to applying said dental bleaching composition.

10. A method as defined in claim 1, said protective composition being applied on or adjacent to the gingival tissue using a syringe.

11. A method as defined in claim 1, further comprising applying said protective composition to said barrier layer and than placing said barrier layer over the tooth surface and gingival tissue to thereby apply said protective composition on or adjacent to the gingival tissue as the barrier layer is placed over the tooth surface and gingival tissue.

12. A method as defined in claim 1, wherein said protective composition is more adhesive than said dental bleaching composition.

13. A method as defined in claim 1, wherein said protective composition comprises a sticky and viscous gel, said barrier layer being placed so as to extend over at least a portion of the gingival tissue in order to protect said protective composition from saliva and/or mechanical forces.

14. A method as defined in claim 1, wherein said protective composition comprises a tissue adhesion agent that is at least one hydrophilic polymer selected from the group comprising polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, and protein.

15. A method as defined in claim 1, wherein said protective composition comprises less than 10% by weight of said dental bleaching agent and wherein said bleaching composition comprises at least 10% by weight of said dental bleaching agent.

16. A method as defined in claim 1, wherein said protective composition further comprises at least one member selected from the group comprising dental desensitizing agents, remineralizing agent, antimicrobial agents, preservatives, antiplaque agents, anti-tartar agents, gingival soothing agents, anesthetics, antioxidants, flavorants, mouth freshening agents, detergents, and colorants.

17. A method as defined in claim 1, wherein said protective composition comprises a flexible polymerizable composition, the method further comprising curing said flexible polymerizable composition.

18. A method as defined in claim 1, wherein said barrier layer comprises a dental tray having at least two sidewalls that define a trough prior to being placed.

19. A method as defined in claim 18, said dental tray being preloaded with said protective composition prior to placing said dental tray.

20. A method as defined in claim 18, wherein said dental tray is thin and flexible, the method further comprising placing said dental tray over the tooth surface by means of a removable exoskeleton.

21. A method as defined in claim 1, wherein said barrier layer is a sheet prior to being placed over the tooth surface.

22. A method of bleaching at least one of a person's teeth, comprising:

prior to applying a moisture-resistant barrier layer, applying a flexible polymerizable composition so as to at least partially cover a person's gingival margin and curing said polymerizable composition;

prior to applying a moisture-resistant barrier layer, applying a dental bleaching composition onto at least one tooth surface, wherein said bleaching composition comprises at least one bleaching agent and a carrier for said bleaching agent;

placing a moisture-resistant barrier layer over the tooth surface in order to protect said bleaching composition from at least one of saliva or mechanical forces; and bleaching the tooth surface by means of said bleaching composition while protecting the gingival tissue near the tooth surface by means of said flexible polymerizable composition.

23. A method as defined in claim 22, said dental bleaching composition and said flexible polymerizable composition each being applied using a syringe.

24. A method of bleaching at least one of a person's teeth, comprising:

prior to applying a moisture-resistant barrier layer, applying a dental bleaching composition onto at least one tooth surface, wherein said bleaching composition comprises at least one bleaching agent and a carrier for said bleaching agent;

providing a moisture-resistant barrier layer that includes a protective composition applied thereto, wherein said protective composition comprises at least one hydrophilic polymer as an oral tissue adhesion agent and is a sticky and viscous gel, and a dental bleaching agent in a lower concentration than the dental bleaching agent contained in said dental bleaching composition;

placing said moisture-resistant barrier layer over the tooth surface and at least a portion of adjacent gingival tissue in order to apply said protective adhesive composition on or adjacent to gingival tissue near the tooth surface in order to form a barrier between the gingival tissue and said bleaching composition and to protect said bleaching composition and protective composition from at least one of saliva or mechanical forces; and bleaching the tooth surface by means of said bleaching composition while protecting the gingival tissue near the tooth surface by means of said protective composition.

25. A kit for providing a dental bleaching composition, a protective composition and a moisture-resistant barrier material for use in practicing the method of bleaching at least one of a person's teeth as defined in any of claims 1-14 or 15-24.

26. A kit as defined in claim 25, wherein the dental bleaching composition comprises a sticky and viscous gel.

27. A kit as defined in claim 25, wherein the protective composition comprises a sticky and viscous gel.

28. A kit as defined in claim 25, wherein the protective composition comprises a flexible polymerizable composition.

29. A kit as defined in claim 25, wherein the barrier layer comprises a dental tray or a substantially flat sheet, strip or patch.

* * * * *

UNITED STATES PATENT AND TRADEMARK OFFICE
CERTIFICATE OF CORRECTION

PATENT NO. : 7,264,471 B2  
APPLICATION NO. : 10/839419  
DATED : September 4, 2007  
INVENTOR(S) : Malcmacher et al.

It is certified that error appears in the above-identified patent and that said Letters Patent is hereby corrected as shown below:

Column 5  
Line 14, change "as tissue adhesive agent" to --as a tissue adhesive agent--

Column 8  
Line 58, change "to the use already" to --to use already--

Column 15  
Line 31, change "Alterntively" to --Alternatively--

Column 18  
Line 19, change "anti-tartar gent" to --anti-tartar agent--  
Line 35, change "of a an alkali metal" to --of an alkali metal--

Column 19  
Line 12, change "over the at least one" to --over at least one--  
Line 46, change "and than placing" to --and then placing--

Signed and Sealed this

Nineteenth Day of August, 2008

JON W. DUDAS  
*Director of the United States Patent and Trademark Office*